US006266428B1

(12) United States Patent
Flanigan

(10) Patent No.: US 6,266,428 B1
(45) Date of Patent: Jul. 24, 2001

(54) SYSTEM AND METHOD FOR REMOTE DETECTION OF HAZARDOUS VAPORS AND AEROSOLS

(75) Inventor: Dennis F. Flanigan, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/024,966

(22) Filed: Feb. 6, 1998

(51) Int. Cl.[7] .......... G06K 9/00
(52) U.S. Cl. .......... 382/100; 250/336.1; 250/341.8
(58) Field of Search .......... 382/109, 125, 382/280, 514, 521, 100, 312, 123; 348/122, 135; 250/341.8, 339.1, 330, 339.14, 338.5

(56) References Cited

U.S. PATENT DOCUMENTS

| | | | | |
|---|---|---|---|---|
| 3,803,609 | * | 4/1974 | Lewis et al. | 343/100 |
| 4,496,839 | * | 1/1985 | Bernstein et al. | 250/341 |
| 4,725,733 | * | 2/1988 | Horman et al. | 250/339 |
| 5,568,186 | * | 10/1996 | Althouse | 348/33 |
| 5,583,972 | * | 12/1996 | Miller | 395/119 |

* cited by examiner

*Primary Examiner*—Joseph Mancuso
*Assistant Examiner*—Yosef Kassa
(74) *Attorney, Agent, or Firm*—Ulysses John Biffoni

(57) ABSTRACT

A first $\Delta^2L$ differential spectral signature spectrum is taken in the field of view at a low spectral resolution. A first linear discriminant optimized for the low spectral resolution is applied to the first spectrum to obtain a first response, and a hazardous cloud is detected automatically in accordance with the first response. A second $\Delta^2L$ differential spectral signature spectrum is taken in the field of view at a higher spectral resolution. A second linear discriminant optimized for the higher spectral resolution is applied to the second spectrum to obtain a second response, which is formed into a false-color image and displayed to an operator. The operator discriminates the hazardous cloud in accordance with the image. The first and second linear discriminants can be formed by linear programming.

23 Claims, 11 Drawing Sheets

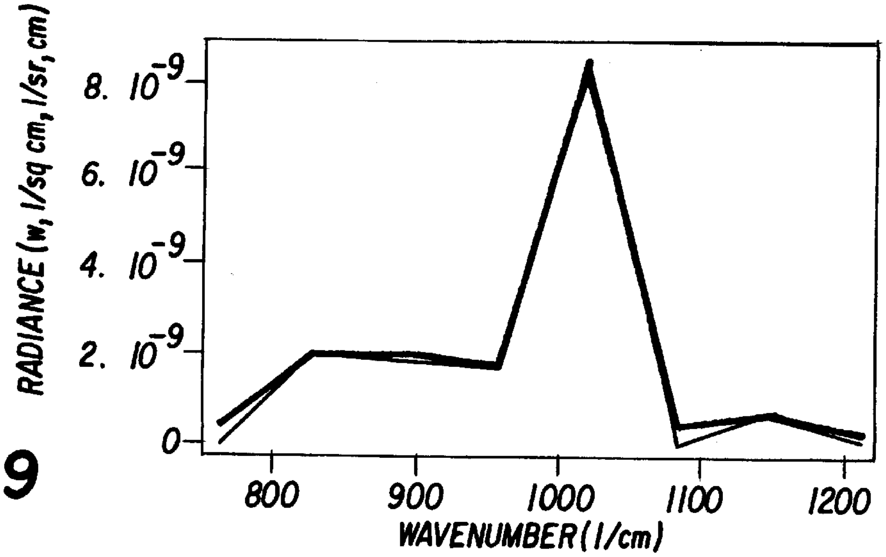
FIG. 9
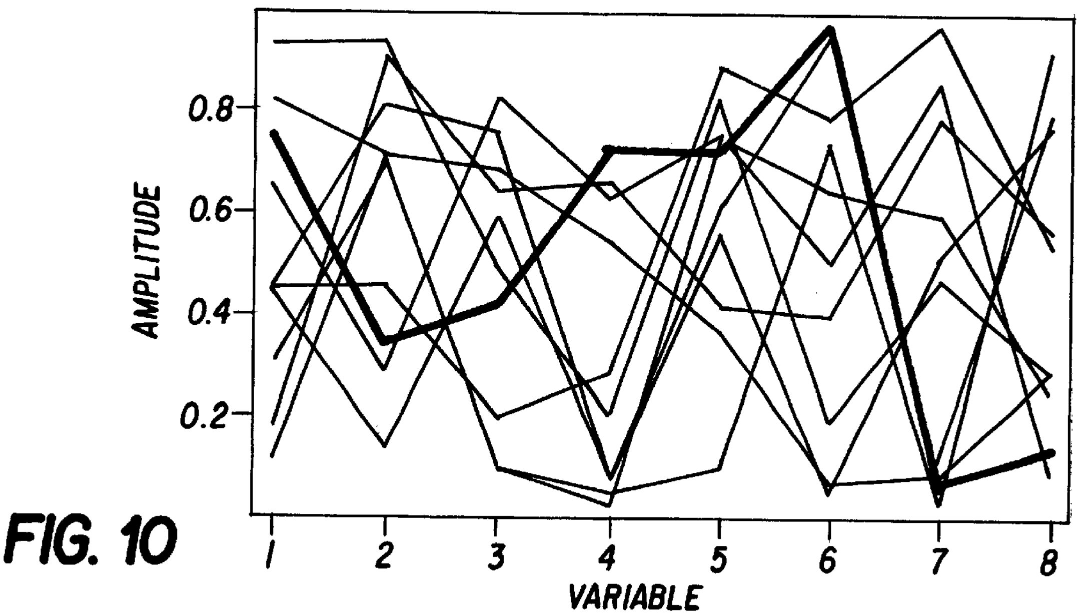
FIG. 10
FIG. 23
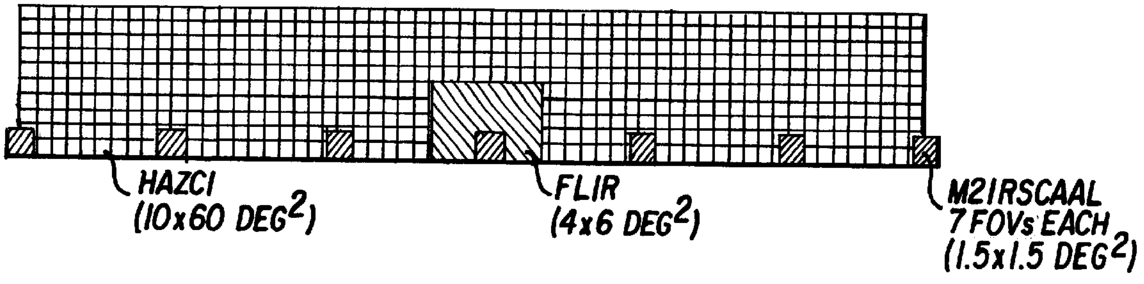

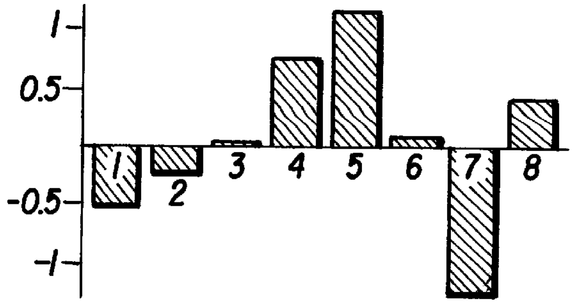
FIG. 11A
FIG. 11B
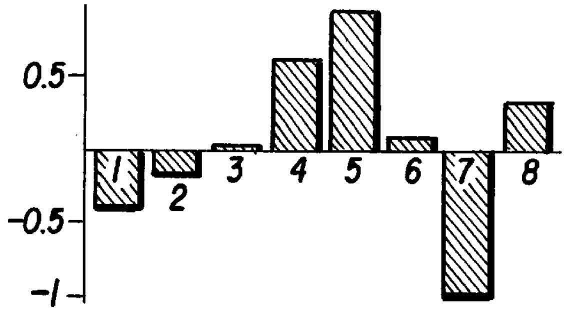
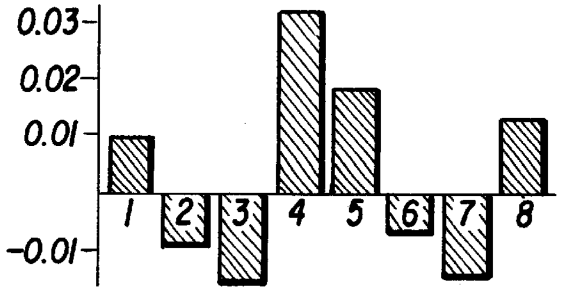
FIG. 11C
FIG. 19
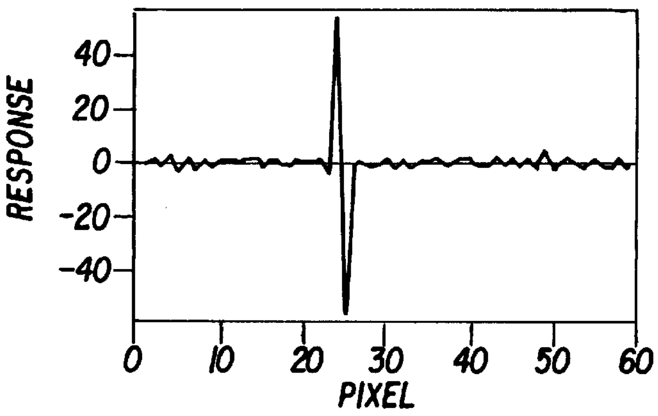

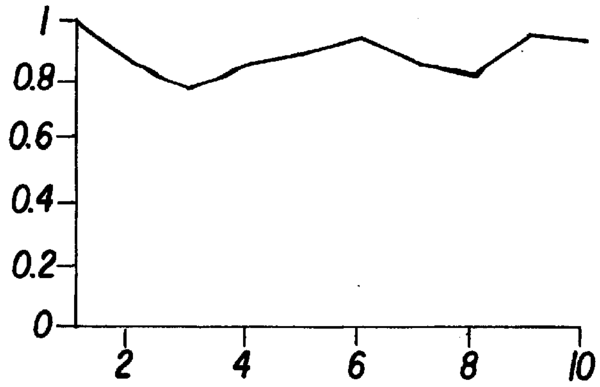
FIG. 12A
FIG. 12B
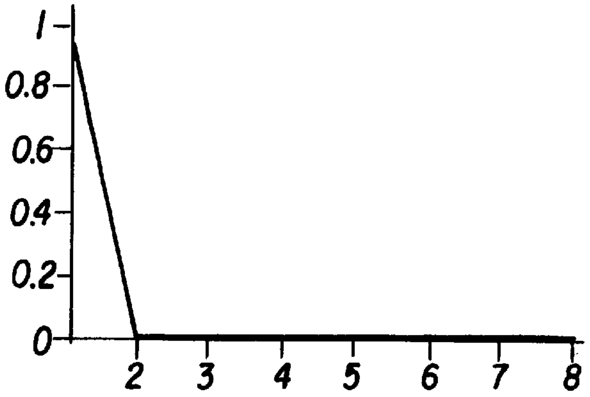
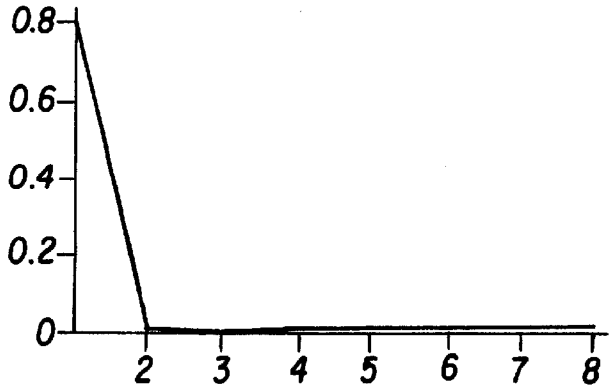
FIG. 12C
FIG. 12D
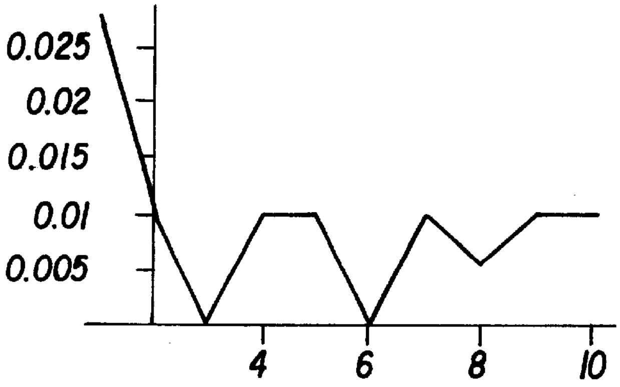

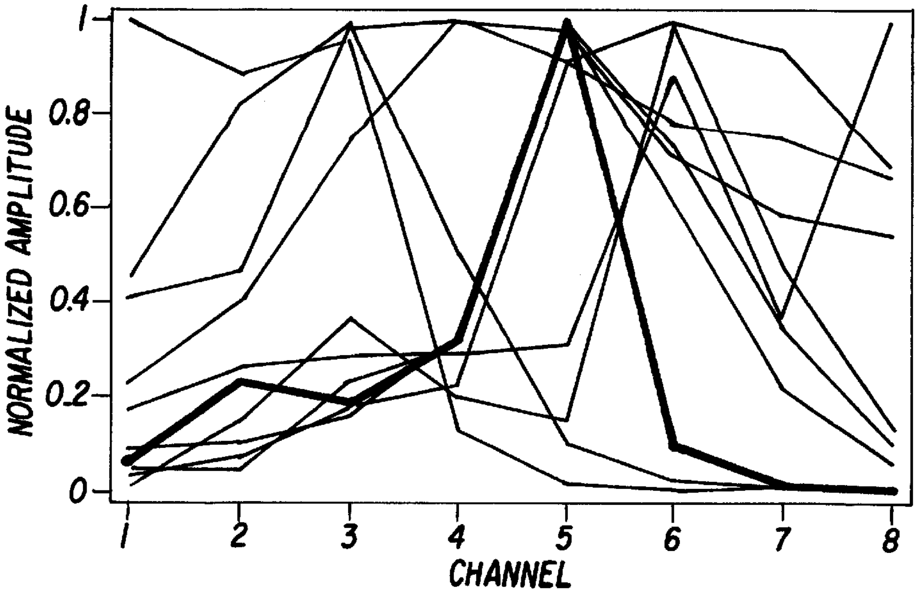
FIG. 13A
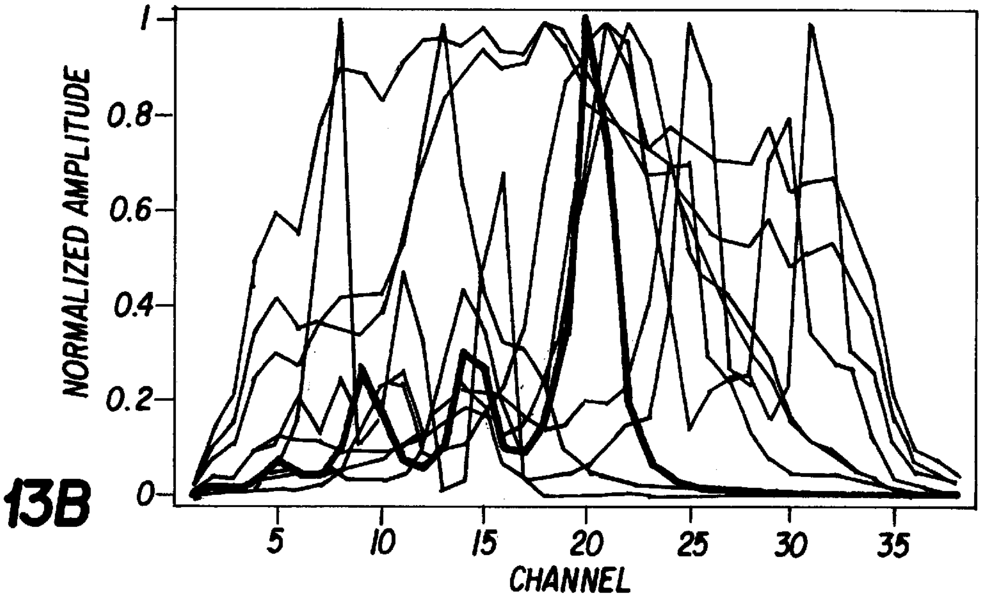
FIG. 13B
FIG. 17A
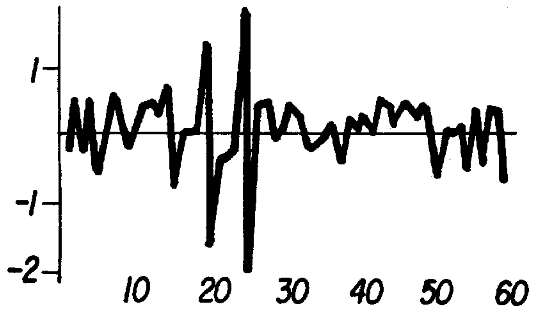
FIG. 17B
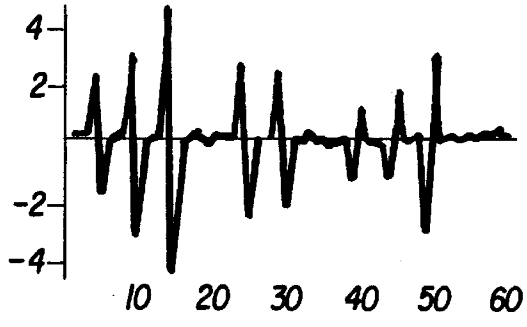

SYSTEM AND METHOD FOR REMOTE DETECTION OF HAZARDOUS VAPORS AND AEROSOLS

GOVERNMENTAL INTEREST

The invention described herein may be manufactured, used, and licensed by or for the U.S. Government.

BACKGROUND OF THE INVENTION

1. Field of the Invention

The invention pertains generally to a system and method for remote detection and warning of hazardous vapors and aerosols and in particular to a system and method for imaging hazardous clouds.

2. Description of Related Art

There are military requirements for the remote detection and warning of chemical warfare vapors and aerosols and a developing civilian need for warning when there is a catastrophic release of a highly toxic compound such as occurred in Bhopal, India. Moreover, there is a general requirement for effective monitoring of chemical clouds, for example, for environmental protection and other reasons. The basic requirement is for warning, i.e., a system that senses and makes a decision without human intervention. Hazardous clouds are amorphous; consequently, the detection and warning systems of the prior art are generally based on spectral characteristics by which it is possible to differentiate between hazardous and non-hazardous clouds. The most developed of the remote sensing passive infrared systems make their decisions based on the integrated energy in a single field-of-view (FOV); i.e., they do not provide an image for interpretation by an operator.

Highly developed passive infrared imaging systems are generally known by the acronym FLIR (Forward Looking Infrared). Thermal infrared FLIR was first demonstrated in the early 1970's. These systems were originally developed for military needs but also have many civilian uses. FLIR's are capable of producing images of many intruder clouds; however, the image is difficult for operators to see when the background is complex or the cloud is larger than the FOV. Even when the cloud is detected, it has proved to be very difficult for the operator to differentiate between threat-simulant clouds and common interferents such as road dust and military screening smokes.

The only operational FLIR for the detection of chemical agents is the Navy's AN/KAS-1, which uses a conventional FLIR modified by the insertion of operator-selectable optical filters to enhance the image contrast for selected compounds such as Sarin. For Army or chemical plant operations, the difficulties of such an approach include: 1) a relatively small FOV, so that the operator must actively search to detect the cloud (a difficult operation in a complex environment unless the operator sees the cloud near its point of origin and can link it with the disseminating source); 2) a very limited capability for the operator to discriminate between chemical hazards and interferents with close spectral signatures, e.g., Sarin and kaolin dust; 3) a limitation to very few similar threats that are spectrally similar; and 4) no automatic capability; the operator must be in the loop at all times.

Conventional passive infrared spectroscopy for the remote detection of chemical agents was first proposed in the 1950's. It was recently brought to fruition with the type classification of the U.S. Army's M21. The M21 uses a conventional Fourier transform infrared (FTIR) sensor to produce a spectrum from which a decision is made on the presence or absence of a chemical agent cloud. In passive infrared spectroscopy, all useful information is contained in a small difference spectrum between the "clean" reference spectrum and the contaminated spectrum.

The M21 uses a conventional procedure to establish a difference spectrum based on measuring and recording a reference spectrum in an assumed clean environment and recursively updating it. The problem has been finding a recursive weight that does not have either too many false alarms or too few detections. (Other suggestions have included the operator swiveling the sensor to an area assumed to be clean and measuring a reference spectrum). The M21 scans seven separate, discontinuous FOV's (each of 1.5° by 1.5° separated by 10° center to center), but does not produce an image. There are several proposed FTIR concepts that use arrays of detectors in the image plane of the interferometer, but these produce relatively conventionally sized images that are insufficiently large to form an image of a realistic threat cloud and/or insufficient étendue (throughput limited by the detector, the interferometer, the collector or the cloud size) for good sensitivity.

Many attempts have been made to bridge the gap between spectral and imaging systems. Traditional solutions generally insert optical filters into FLIR systems to enhance spectral discrimination. More recently, the single detector in the FTIR sensor has been replaced by a square array of detectors to enhance imaging capability. These solutions have had limited success because the sensors were optimized for different objectives with different constraints.

Passive spectroradiometers operate from a temperature difference, $\Delta T$, between the target cloud and the background. Natural temperature differences are generally very small, from a fraction of a °K to a few °K; therefore, achieving optimum performance is a very demanding problem. Sensitivity, i.e., the detection of minimum quantities, is a function of spectral resolution and scan time, it can be increased by either decreasing the spectral resolution and/or increasing the scan time. However, there are negative aspects to both of these approaches. With decreased spectral resolution there are increased problems of discrimination between target materials and interferents. With increased scan time there is less warning time. Resolution and scan time for automatic warning systems, such as the Army's M21, are generally fixed at the time of the design.

Conventional passive infrared detection and warning systems fix the resolution of the sensor and scan time at a value appropriate for laboratory analysis. This compromises both sensitivity and discrimination, i.e., the ability to differentiate between chemical agents. Differential signatures are formed by subtracting an internal infrared source (which does not maximize the signature of the threat) from the incoming signature or by subtracting a reference signature, measured at some earlier time at the same spatial position, from the incoming signature (which limits real time and mobile operation). A single resolution linear discriminant is used for both detection and discrimination.

Conventional methods of spectral detection and discrimination rely on a single linear discriminant applied to the difference spectrum. (This is an operation that is much more effectively done by a machine.) Sensitivity and discrimination are critically dependent on spectral resolution in an inverse way. The M21 is limited in sensitivity by its choice of a single conventional resolution of 4 $cm^{-1}$, far higher than necessary for the detection of chemical agents.

The "fitting" of linear discriminants to the problem of detection and discrimination can be accomplished by many techniques; however, the various methods do not necessarily lead to the same result. Conventional methods of computing linear discriminants rely for the most part on "training" techniques ranging from linear regression to neural networks. Such training methods are very time-consuming and do not necessarily converge to a solution guaranteed to classify even known interferents properly; results depend not only on the training program, but also on how often the data are presented to the training program.

SUMMARY OF THE INVENTION

An object of the invention is to provide a system and method for remote detection of hazardous clouds (vapors and aerosols) that avoids the above-noted deficiencies of the related art.

To achieve this and other ends, the present invention is directed to a method of detecting and discriminating a hazardous cloud in a field of view, the method comprising: (a) forming a first linear discriminant for detecting the hazardous cloud at a first spectral resolution and a second linear discriminant for discriminating the hazardous cloud at a second spectral resolution which is higher than the first spectral resolution; () detecting the hazardous cloud by (i) taking a first $\Delta^2L$ spectrum, i.e., a differential spectral signature as defined by D. F. Flanigan, "Prediction of the limits of detection of hazardous vapors by passive infrared by the use of MODTRAN," Applied Optics, Vol. 35, No. 30, October 1996, hereby incorporated by reference, in the field of view at the first spectral resolution, (ii) applying the first linear discriminant to the first $\Delta^2L$ spectrum to obtain a first response, and (iii) detecting whether the hazardous cloud is present in accordance with the first response; and (c) if the hazardous cloud is detected to be present in step (b)(iii), discriminating the hazardous cloud by (I) taking a second $\Delta^2L$ spectrum in the field of view at the second spectral resolution, (ii) applying the second linear discriminant to the second $\Delta^2L$ spectrum to obtain the second response; and (iii) discriminating the hazardous cloud in accordance with the second response.

The present invention is further directed to a system for detecting and discriminating a hazardous cloud in a field of view, the system comprising: detector means for (i) taking a first $\Delta^2L$ spectrum in the field of view at a first spectral resolution and (ii) taking a second $\Delta^2L$ spectrum in the field of view at a second spectral resolution which is higher than the first spectral resolution; signal processor means, said processor means storing a first linear discriminant for detecting the hazardous cloud at a first spectral resolution and a second linear discriminant for discriminating the hazardous cloud at a second spectral resolution which is higher than the first spectral resolution, for (i) detecting the hazardous cloud by applying the first linear discriminant to the first $\Delta^2L$ spectrum to obtain a first response and detecting whether the hazardous cloud is present in accordance with the first response and (ii) if the hazardous cloud is detected to be present, discriminating the hazardous cloud by applying the second linear discriminant to the second $\Delta^2L$ spectrum to obtain the second response and discriminating the hazardous cloud in accordance with the second response; and interface means for communicating to an operator a result of detecting and discriminating the hazardous cloud.

The invention uses a spatial scan (typically a horizontal scan followed by a vertical shift) to produce an array of differential spectral signatures based on measuring infrared radiance between adjacent pixels and taking a second-order differential, $\Delta^2L$, between the infrared radiances of adjacent pixels. A linear discriminant is applied to the spectrum for each pixel to produce a two-dimensional array of false colors that are plotted as an image. A two-step resolution process is used for detection and discrimination. A synergistic combination of automatic detection and user discrimination is involved in the two-step process. Infralow resolution is used to enhance detection sensitivity. Linear programming is used to calculate the coefficients of the discrimination linear discriminant (used in imaging).

The invention is based on optimizing a spectral imager for the purpose of hazardous cloud detection and warning. The system and method according to the invention optimize both spectral and spatial resolution for hazardous cloud imaging and provide for combined automatic and operator detection and warning, each doing what it does best. A spatially scanning sensor with both variable resolution and variable scan time is controlled by the signal processor in a 2 step process. Maximum detection sensitivity would be achieved by using infralow (below low) resolution, perhaps as low as 64 $cm^{-1}$, with fast scan times of 1/60 second or less per pixel to form an array of differential ($\Delta^2L$) spectral signatures. These $\Delta^2L$ signatures are operated on by linear discriminants (LD) to produce a plottable array of"false color" numbers. When an intruder cloud is detected by a decision algorithm (generally based on preset alarm values), the signal processor or operator switches to higher resolution and longer scan times for imaging of only the threat cloud which the operator interprets for maximum detection and minimum false alarms The invention makes use of a differential spatial scanning concept to produce an array of difference ($\Delta^2L$) spectral signatures that contain only the information needed for the detection and identification of hazardous vapors or aerosols. Multiple spectral resolutions are used: infralow for detection and higher (but still low by comparison with laboratory standards) for identification. Multiple linear discriminants are used, each optimized for a different role. These multiple linear discriminants can be used to produce values for plotting an image. The linear discriminants can be calculated by the use of linear programming.

The present invention finds utility in the imaging of clouds composed of hazardous vapors or aerosols in situations where a high level of importance is placed on detection and warning, such as chemical warfare defense or protection of civilians in the wake of chemical plants. The invention finds further utility for emergency management in hazardous spills and for monitoring suspected terrorist activities, drug processing, and chemical manufacturing.

The invention provides for real-time imaging of hazardous vapor and aerosol clouds from a sensor mounted on either a static or moving platform. The invention capitalizes on a synergistic combination of the respective strengths of the human operator and the machine.

The invention involves subtracting adjacent (or near adjacent) pixels in a scanned horizontal arc (to take advantages of the known properties of low angle sky). It is based on the fact that incipient hazardous clouds are very non-uniform.

The invention allows for scanning a very wide area with compensating low spatial resolution for good detection sensitivity. The very large area will almost guarantee that there are significant variations in the perceived CL (chemical concentration multiplied by cloud length) of the cloud that will enable the operator to determine the extent and general form of the cloud. The proposed method detects with a linear discriminant and, based on the result, forms an image of suspect clouds and issues an automatic warning. The proposed method is also likely to highlight other characteristics of the image, such as transitions between types of backgrounds or man-made structures, for which it might be difficult to find a universal discrimination algorithm. Such complications can be handled by the operator. (Humans find it much easier than machines to deal with spatial patterns.)

The invention uses a two-step process based on two resolutions: one ideal for detection and one for identification. In an illustrative example given below, resolutions of 64 $cm^{-1}$ and 16 $cm^{-1}$ were selected for detection and discrimination respectively. (These are much lower than in conventional practice.) There are two separate linear discriminants for simultaneously detecting each compound of interest. The use of such two separate linear discriminants is easily accomplished with programming.

Linear programming, as used in the invention, converges to a solution guaranteed to classify the threat and known interferents properly, although they are limited by fuzzy changes and noise. The fitting process is very fast.

BRIEF DESCRIPTION OF THE DRAWINGS

The invention will now be set forth in detail with reference to the drawings, in which:

FIG. 9 shows the same signature as in FIG. 4, except at a resolution of 64 $cm^{-1}$;

FIG. 10 shows ten signatures generated with a pseudo-random number generator;

FIG. 11A shows coefficients obtained by solving simultaneous linear equations for eight of the signatures shown in FIG. 10;

FIG. 11B shows coefficients obtained through linear programming from the same eight signatures;

FIG. 11C shows coefficients obtained through linear programming from all ten signatures shown in FIG. 10;

FIG. 12A shows the correlation of the threat signature of FIG. 10 with the nine interferant signatures of FIG. 10;

FIG. 12B shows the response curve for the solution to simultaneous equations for eight variables and eight signatures;

FIG. 12C shows the response curve for the linear programming solution for eight variables and the same eight signatures;

FIG. 12D shows the response curve for the linear programming solution for eight variables and all ten signatures;

FIG. 13A shows normalized $\Delta^2L$ spectra for Sarin and a variety of interferents at a resolution of 64 $cm^{-1}$;

FIG. 13B shows the same spectra at a resolution of 16 $cm^{-1}$;

FIG. 17A shows the response given by application of the linear discriminant of FIG. 14A to the spectral radiance shown in FIG. 16;

FIG. 17B shows the response given by application of the linear discriminant of FIG. 14B to the spectral radiance shown in FIG. 16;

FIG. 19 shows the response for the differential spectral radiance shown in FIG. 18;

FIG. 23 shows comparative fields of view of the apparatus of FIG. 20 and two apparati of the prior art.

DETAILED DESCRIPTION OF THE INVENTION

At the outset, it will be useful to describe the advantages of infralow resolution for detection. Once these advantages have been described, the specifics of the system and method implementing such infralow resolution will be described.

Most organic vapors and aerosols and biological clouds have unique spectral signatures in the 700 $cm^{-1}$ to 1300 $cm^{-1}$ (8 $\mu$m to 14 $\mu$m) infrared region of the electromagnetic spectrum. Detection and warning require detection of these signatures and differentiation of these signatures from those of non-hazardous interferents. A sensor, generally an FIR, is used to provide the signatures, and a signal processor is used to decide whether hazardous vapors or aerosols are present.

In conventional IR spectroscopy, resolution levels are generally understood to be high when the half height bandwidth (HHBW) is less than 1 $cm^{-1}$ (frequently much less). Such high resolution is usually necessary only for the analysis of gases with fine structure. Medium resolution, 2 $cm^{-1}$ to 4 $cm^{-1}$, is used for the qualitative analysis of solutions or organic vapors. Low resolution, 10 $cm^{-1}$ and up, improves the speed and accuracy of quantitative analysis.

Figure 1:
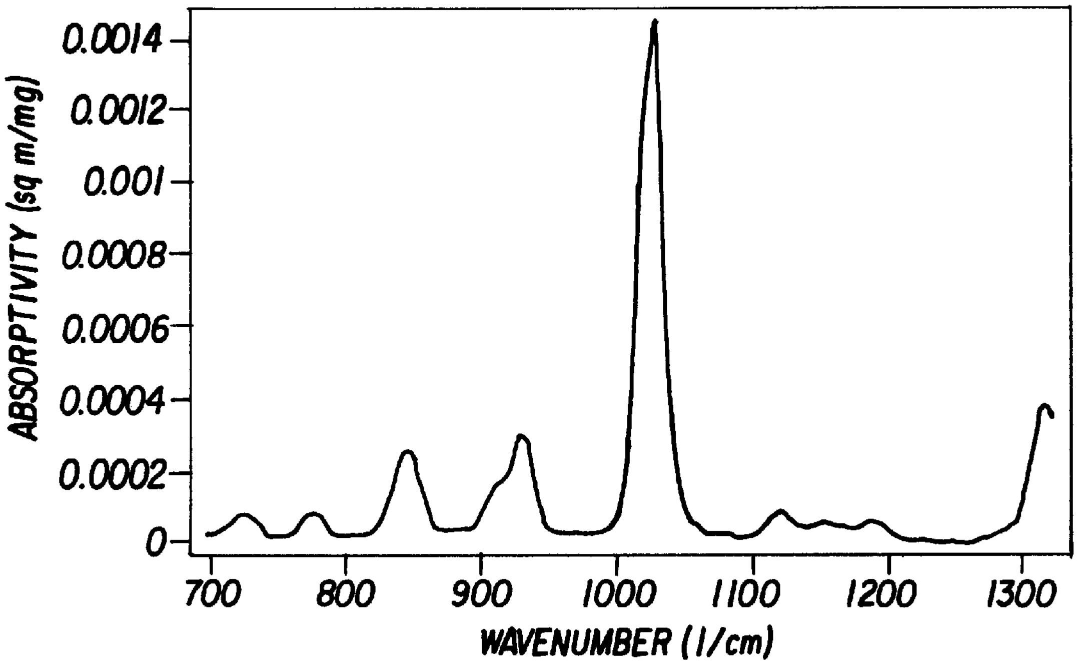
FIG. 1 shows the vapor-phase absorptivity of Sarin.

FIG. 1 shows the absorptivity of Sarin, which does not have fine structure. The HHBW of the 1024 $cm^{-1}$ band is about 21 $cm^{-1}$, approximately 50% wider in the vapor than in solution.

Figure 2:
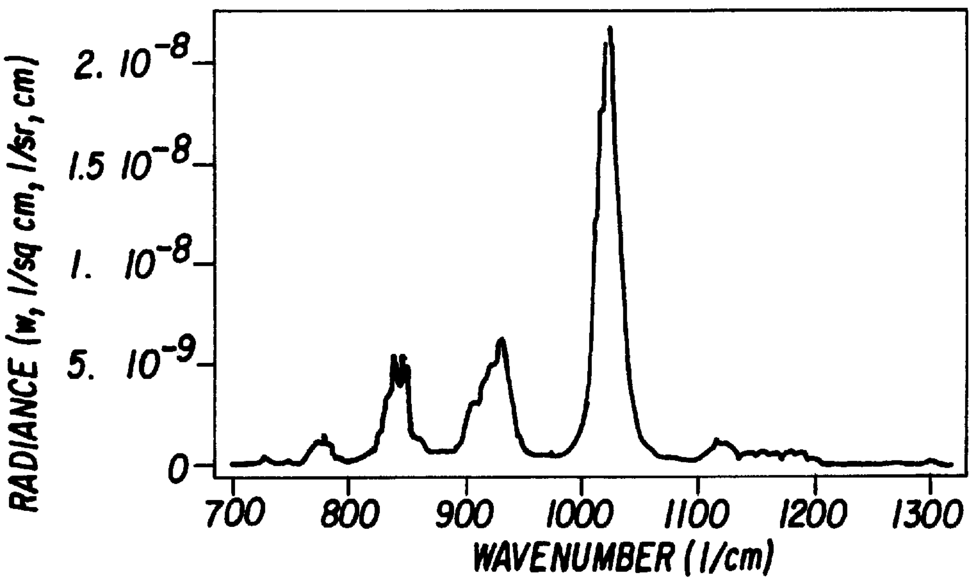
FIG. 2 shows an atmospheric signature of Sarin at a resolution of 2 $cm^{-1}$.
Figure 3:
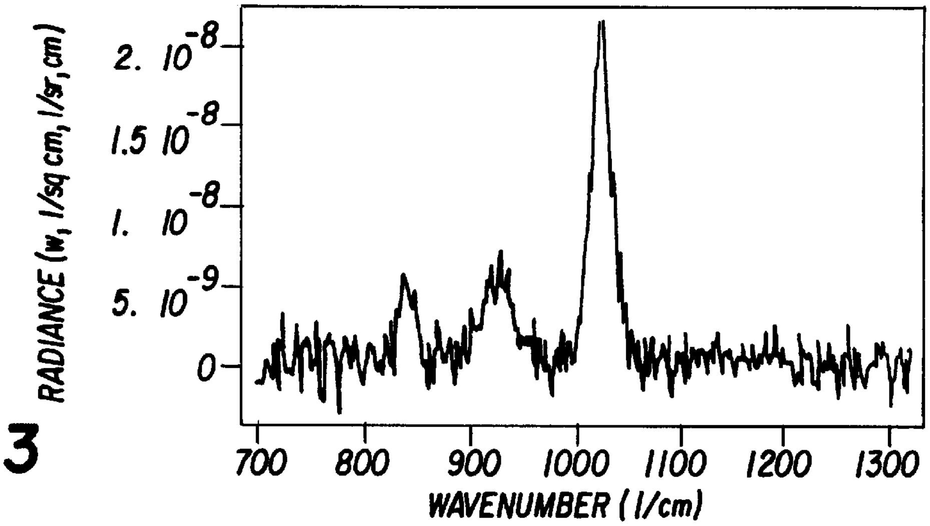
FIG. 3 shows the same signature as in FIG. 2, except with noise appropriate for a 1 second measurement time.

$\Delta L$ has been defined in the art as a measure of potential to detect an intruder cloud; $\Delta^2L$ has been defined in the art as the difference between radiances actually induced by the cloud. The $\Delta^2$L spectrum is simulated using a 3-layer model. The background and atmospheric transmittance are calculated with software such as MODTRAN and combined with the intruder vapor spectrum in a Mathematica program or other suitable software. Noise, consistent with sensor performance, resolution and measurement time, is added with a pseudo random number generator. FIG. 2 shows the $\Delta^2$L signature of 100 mg/m$^2$ of Sarin at a distance of 1 km with the US Standard atmospheric model at a resolution of 2 cm$^{-1}$. The fine structure riding on the lesser Sarin bands, from 700 cm$^{-1}$ to 900 cm$^{-1}$, is due to fine lines from atmospheric species. FIG. 3 is the same signature as FIG. 2 except with noise contributed by a detector noise limited Fourier transform spectrometer (FTS) with a 1 second measurement time. The estimated signal-to-noise ratio (SNR) is better than five, which is adequate for reliable detection. If the available measurement time is only 1/60 second, all other conditions remaining the same, the signature is no longer visible over the noise, as shown in FIG. 4.

Figure 4:
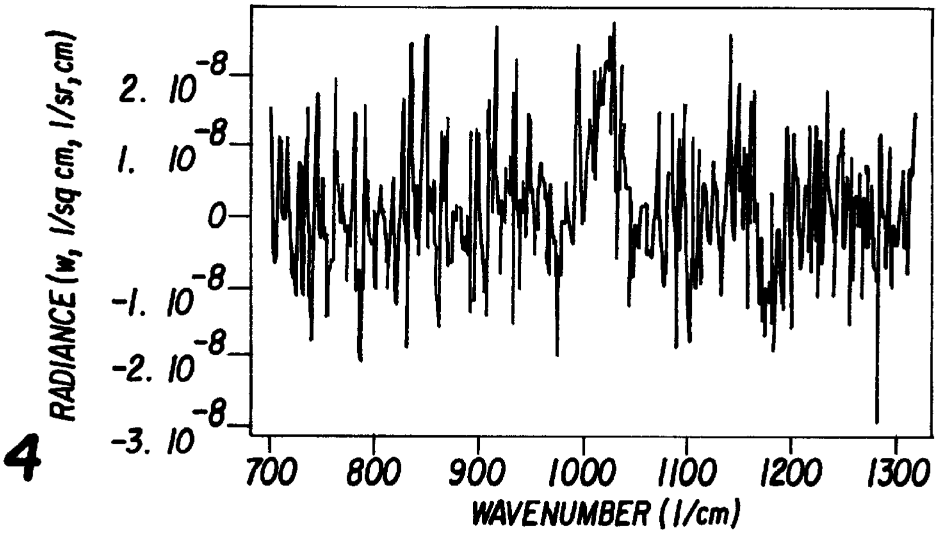
FIG. 4 shows the same signature as in FIG. 2, except with noise appropriate for a 1/60 second measurement time.
Figure 5:
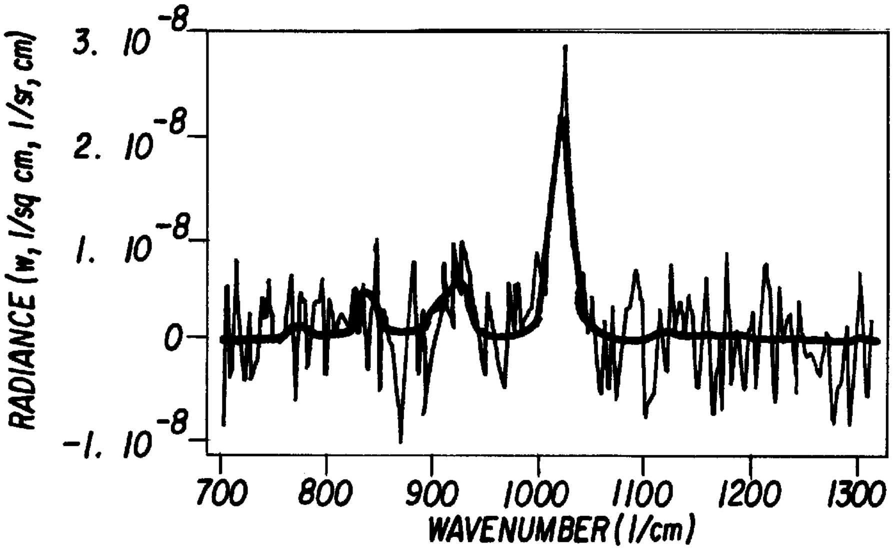
FIG. 5 shows the same signature as in FIG. 4, except at a resolution of 4 $cm^{-1}$.
Figure 6:
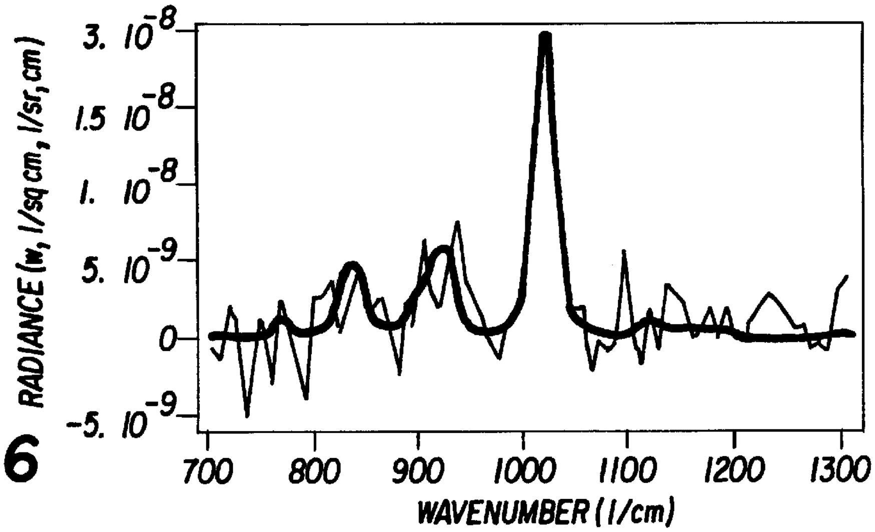
FIG. 6 shows the same signature as in FIG. 4, except at a resolution of 8 $cm^{-1}$.
Figure 7:
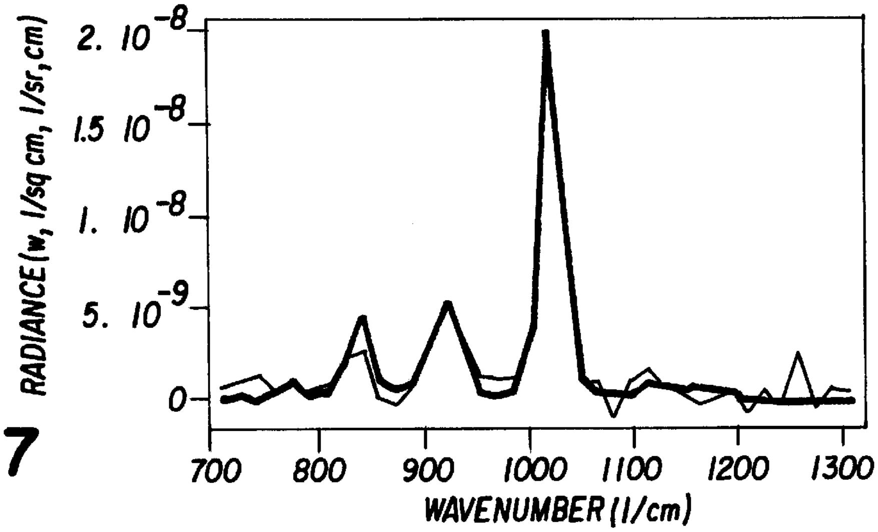
FIG. 7 shows the same signature as in FIG. 4, except at a resolution of 16 $cm^{-1}$.
Figure 8:
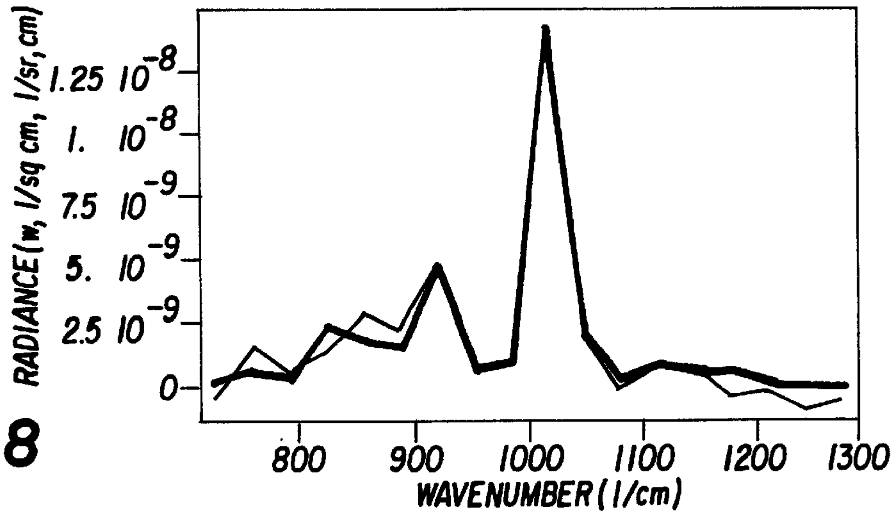
FIG. 8 shows the same signature as in FIG. 4, except at a resolution of 32 $cm^{-1}$.

The effect of lowering the resolution of the sensor on the spectrum shown in FIG. 4 will now be considered. FIGS. 5–9 show the same spectrum as in FIG. 4, except with the following resolutions:

| Figure | Resolution |
|---|---|
| 5 | 4 cm$^{-1}$ |
| 6 | 8 cm$^{-1}$ |
| 7 | 16 cm$^{-1}$ |
| 8 | 32 cm$^{-1}$ |
| 9 | 64 cm$^{-1}$ |

In each of FIGS. 5–9, the thick line shows the spectrum without noise, and the thin line shows the same spectrum with noise. These figures show that all the Sarin spectral features are clear at 16 cm$^{-1}$ and that the main feature is detectable at 64 cm$^{-1}$. It is not until the resolution has been reduced to 128 cm$^{-1}$ (not shown) that all Sarin spectral features "wash out."

FIG. 9 shows that the noise level is the lowest at 64 cm$^{-1}$ resolution. In this example, 64 cm$^{-1}$ resolution will be used in the detection mode, and 16 cm$^{-1}$ will used in the discrimination mode. This infralow resolution effect on detection has been discovered in simulating spectra; it was not readily apparent from the equations. The effects are most easily visualized in a dynamic simulation. However, one can easily imagine the effect of the "thin line" randomly varying about the "thick line," in FIGS. 4 through 9, keeping in mind that the excursions generally stay within an envelope suggested by the thin line.

Experience shows that the problem of discrimination can be dealt with by assuming two types of change. There are well defined spectal changes that can be attributed to spectral interferents such as kaolin dust, and there are "fuzzy" changes due to underlying shifts in the background temperature and concentration changes of atmospheric species with features below the spectral resolution of the sensor. Linear discriminants (LD's), computed with linear programming techniques, work rather well to discriminate between species based on their spectral properties. LD's are generally precomputed when the threat and interferant spectra are known a priori. The fuzzy problem is conventionally handled by measuring an assumed clean background, recursively updating that background, and subtracting it from the current measured background. Not only is the recursive background technique somewhat clumsy for moving operation, but it has also proved difficult to find a satisfactory recursive weight between too many false alarms and "learning" the spectrum of the threat gas. A differential scan approach, to be described has the potential to handle fuzzy changes without these constraints.

The linear discriminant function will now be described. The response R to a multivariate signal $\{S_1, S_2, \ldots S_n\}$ is $$R = c_1 s_1 + c_2 s_2 + \ldots + c_n s_n = \sum_{i=1}^{n} c_i s_i \qquad (1)$$

where $\{c_1, c_2, \ldots c_n\}$ is a set of coefficients chosen such that the incoming signatures are separated into at least two classes, namely, threat and interferant. The operation shown in Equation (1) is known as an inner product or as a dot product. The fitting of the set of coefficients $\{c_1, c_2, \ldots c_n\}$ to such separation is done with linear programming.

Simultaneous equations produce coefficients that are a deterministic solution to the problem of separating signatures, but they require exactly n equations for n variables, in this case, n optical channels. Linear programming produces coefficients that are also deterministic; the advantage is that the method is quite flexable in the number of equations that it will accept. It will be shown below that the two methods produce the same results in the limiting case where the number of variables and the number of equations are equal. Linear programming will then be extended to cases where simultaneous equation methods cannot be applied. Ten signatures were generated using a pseudo-random number generator at eight variables. These signatures are shown FIG. 10. (These are treated as deterministic although they were generated with a random number generator for convenience.) The signature shown as thick in FIG. 10 is defined as the threat, and all the other signatures are defined as the interferents.

To form the simultaneous equations, the dot product of Equation (1) is set to one for the threat (indicated without superscripts) and to zero for signatures 2 through 8 for the first seven interferents (indicated by superscripts 2 through 8):

$$c_1s_1+c_2s_2+\ldots+c_8s_8=1$$

$$c_1s_1^2+c_2s_2^2+\ldots+c_8s_8^2=0$$

$$\ldots$$

$$c_1s_1^8+c_2s_2^8+\ldots+c_8s_8^8=0 \qquad (2)$$

Those skilled in the art will appreciate that the solution to set of equations (2) is a form of orthogonalization. That is, a vector c in eight-space (or as many dimensions as needed) having components $\{c_1, c_2, \ldots c_8\}$ is sought to be perpendicular to the vectors for all interferents, namely, vectors $s^2=\{s_1^2, s_2^2, \ldots s_8^2\}$ through $s^8=\{s_1^8, s_2^8, \ldots s_8^8\}$, but not to be perpendicular to the vector for Sarin, namely, $s^2=\{s_1, s_2, \ldots s_8\}$. In this notation, set of equations (2) becomes $c\cdot s=1$, while $c\cdot s^2=\ldots=c\cdot s^8=0$.

Set of equations (2) can be solved by any suitable operation for solving simultaneous equations, such as the Mathematica program "LinearSolve." Such a solution provides the coefficients shown in FIG. 11A.

The same set of equations can be solved through linear programming by maximizing the response of the target signature, namely, $c\cdot s=c_1s_1+c_2s_2+\ldots+_8c_8s$, subject to the following constraints on the responses for interferents 2–8:

$$c_1s_1^2+c_2s_2^2+\ldots+c_8s_8^2=c\cdot s^2\leq k$$

$$c_1s_1^8+c_2s_2^8+\ldots+c_8s_8^8=c\cdot s^8\leq k \quad (3)$$

However, linear programming programs are normally used in resource problems where negative variables have no meaning In this problem, negative coefficients are required; therefore, a coordinate transformation is required to get a solution, and then another transformation is required to get back to the coefficient space. The desired coefficient space is −1 to +n. The following transformation will achieve coefficients ranging from 0 to n:

$$c_1s_1^2+c_2s_2^2+\ldots+c_8s_8^2=c\cdot s^2\leq k+\sum_{n=1}^{8}s_n^2 \quad (4)$$

$$c_1s_1^2+c_2s_2^2+\ldots+c_8s_8^2=c\cdot s^2\geq \sum_{n=1}^{8}s_n^2$$

$$\ldots$$

$$c_1s_1^8+c_2s_2^8+\ldots+c_8s_8^8=c\cdot s^8\leq k+\sum_{n=1}^{8}s_n^8$$

$$c_1s_1^8+c_2s_2^8+\ldots+c_8s_8^8=c\cdot s^8\geq \sum_{n=1}^{8}s_n^8$$

If −1 is added to each coefficient, the resulting set generally ranges from −1 to 20 for most practical problems. Setting k=0.01 and solving by the set with the Mathematica program “ConstrainedMax” obtained the set of coefficients shown in FIG. 11B. Comparison of FIGS. 11A and 11B shows that the coefficients computed by the two methods are very similar in shape and quantity for eight signatures, but not identical. FIG. 11C shows the coefficients when the final two signatures in FIG. 10 are added. Not only is the solution different in shape, but also, the coefficients are much smaller. A comparison of the performance of the coefficients shown in FIG. 11 with the signatures shown in FIG. 10 is shown in FIGS. 12A–12D. FIG. 12A shows the correlation of the threat signature with the nine interferant signatures. FIG. 12B shows the response curve for the solution to simultaneous equations (2) for eight variables and eight signatures. FIG. 12C shows the response curve for the linear programming solution for eight variables and the same eight signatures. FIG. 12D shows the response curve for the linear programming solution for eight variables and all ten signatures.

First the threat signature was correlated with the other nine signatures, namely, the interferant signatures. FIG. 12A shows that there is a high degree of correlation between signatures. Comparison of the response curves of FIGS. 12B and 12C shows that the simultaneous-equation solution does produce one for the first spectrum and essentially zero (there was a very small residual) for signatures 2 through 8. The response of the linear programming solution to the threat signature is about the same, and the response to signatures 2 through 8 is held within the required value of 0.01 (barely more than the thickness of the thick line). FIG. 12D, the response for all ten signatures, shows that the response to the interferents has been constrained to 0.01 or less, but also shows a marked drop in the response to the target signature.

From these numerical experiments, several properties of the linear programming solutions can be observed. First, each unique signature generally benefits from an additional variable (spectral channel) for good separation of the threat signature. Even then, much depends on chance; occasionally, good separation is obtained with ten signatures and only eight variables. Second, over many experiments, the relative performance of the coefficients produced by simultaneous equations and linear programming could vary either way, usually within about 30%. Third, the variation in the number of positive coefficients is a measure of the complexity of the separation problem. In theory, a linear program can be set up to separate in many classes by choosing the constraints carefully; in practice, there is probably no linear solution in most of these cases.

In light of the foregoing discussion, a practical detection and discrimination problem will be considered. FIGS. 13A and 13B show the normalized $\Delta^2$L spectra for Sarin (dark line), three dusts (kaolin, illite, montmorillonite), four smokes (white phosphorus (WP), HC vapor, HC particulate and soot), agent orange, and a vapor component of DS2 (a decontaminating agent used in military operations) methyl cellosolve. FIG. 13A is at 64 $cm^{-1}$ resolution, and FIG. 13B is at 16 $cm^{-1}$ resolution. The problem is to find a first LD for optimum detection of Sarin at 64 $cm^{-1}$ resolution and a second LD for optimum discrimination at 16 $cm^{-1}$ resolution.

The infralow (first step) LD can be can be optimized for either detection or discrimination. The LID shown in FIG. 14A resulted from applying linear programming to all of the signatures shown in FIG. 13A. As a measure of discrimination, this LD produced a response ratio of Sarin to kaolin of three. The LD shown in FIG. 14B was chosen by inspection of FIG. 13A to produce the maximum response to Sarin without regard to its response to the interferents. The second-step LD (always chosen for discrimination capability) shown in FIG. 15 resulted from applying linear programming to the signatures shown in FIG. 13B. The Sarin to kaolin response ratio was 45. The optimum discriminating ED computed for the 64 $cm^{-1}$ resolution signatures appears to be similar in general qualitative form to the LD's computed earlier for the random signature problem. On the other hand, the LD for the 16 $cm^{-1}$ resolution appears much different in form and magnitude; there are only eight positive coefficients out of 38. This can be interpreted as a consequence of saturating the discriminating capability of the infralow resolution LD while there is still discriminating potential remaining at the merely low resolution of 16 $cm^{-1}$. This is consistent with the earlier observation that the number of variables needed for good discrimination performance is roughly equal to the number of independent signatures in the problem.

Most of the spectral information needed to detect and identify is found within the $\Delta^2$L spectrum. In contrast, the ΔL spectrum contains considerable atmospheric structure which interferes with the detection of the subtle changes introduced by the threat cloud. While the ΔL spectrum can be unambiguously established by subtracting the incoming radiance from a ambient temperature blackbody, the $\Delta^2$L spectrum must be established from clean and contaminated backgrounds. Inasmuch as it is not known a priori which backgrounds are clean and which are contaminated, an alternative search model is needed. If the intruder cloud is to form an image, it cannot be uniformly distributed across the entire FOV. In practice, if the search area is very large, say, an azimuth range of 60° (at per-pixel resolution of 1°) or greater, it should be very rare to have a uniformly contaminated scene from an incipient intruder cloud. In most practical situations, scanning a large arc would produce not only a cloud edge, but also significant CL variations. This suggests an approach based on spatial differences; the $\Delta^2$L spectrum need only be the result of a difference between radiance in different pixels.

It is known that the thermal IR sky background spectrum does not change or, at the most, does not change strongly with azimuthal angle, but decreases strongly with angle of elevation (AOE). Therefore, a horizontal scan should produce an essentially unchanging $\Delta^2L$ spectrum (in the absence of intruder cloud or an intervening object), while a vertical scan would produce a $\Delta^2L$ spectrum with strongly modulated atmospheric species. Moreover, $\Delta L$ strongly increases with AOE; but, under most important threat situations, the CL of the threat vapor is likely to decrease strongly with AOE. This would suggest scanning horizontal arc at increasing AOE's to produce an image; as an illustrative example, this disclosure will consider the case of 1° AOE to produce one line of a raster scan.

The are complications with a spatial scan. Intervening objects or background transitions will also produce discontinuities in the signature, e.g., going from clear sky to cloudy sky or to terrain, vehicles, trees, etc. It seems likely that many of these changes will create signatures that resemble $\Delta L$ spectra, thereby creating strong spectral features by which they can be rejected by a discrimination algorithm. Other changes may develop spatial criteria by which they can be recognized by an operator. However, for simplicity, it win be assumed in this example that the FOV is completely low-angle-sky.

Figure 16:
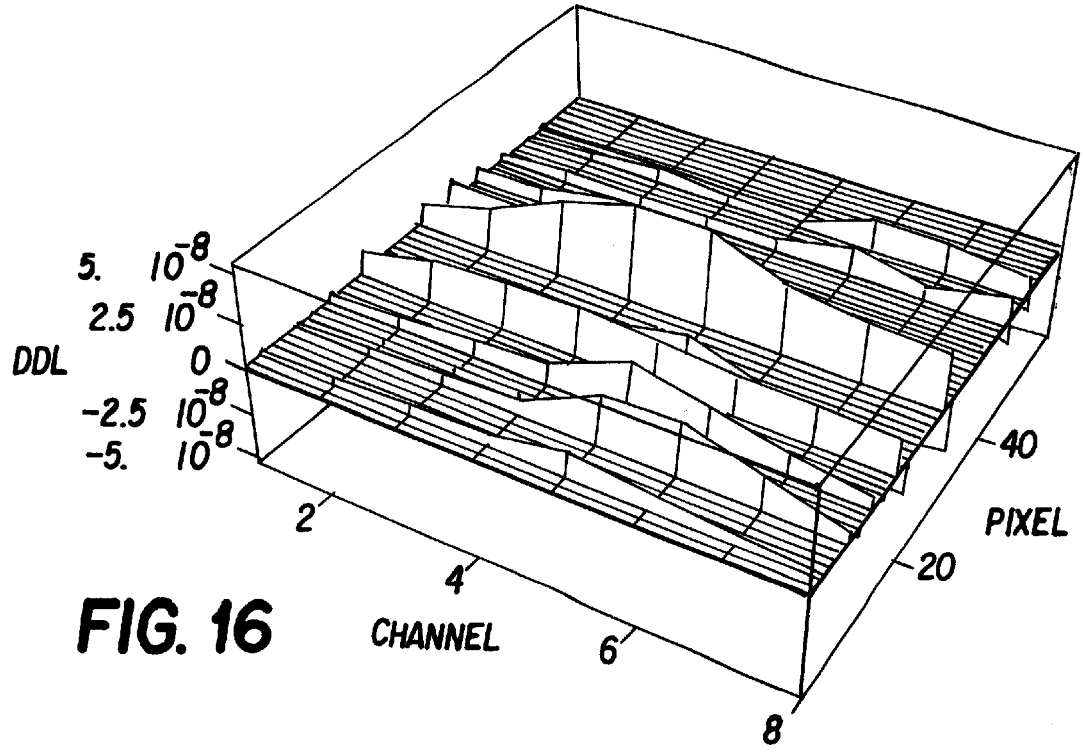
FIG. 16 shows a differential spectral radiance for a mixture often compounds and Gaussian spectral noise for 59 FOV's at a resolution of 64 $cm^{-1}$ and a measurement time of 1/60 sec.

A horizontal arc of 60 contiguous pixels with a clear, low-angle sky background will be considered. FIG. 16 shows 59 $\Delta^2L$ spectra at the infralow resolution of 64 $cm^{-1}$ with Gaussian distributed random noise appropriate to a 1/60 sec measurement time. The $\Delta^2L$ signature for one of 10 compounds is inserted every 5th pixel:

| Pixel | Compound |
|---|---|
| 5 | kaolin |
| 10 | montmorillonite |
| 15 | illite |
| 20 | soot |
| 25 | Sarin |
| 30 | WP smoke |
| 35 | HC vapor |
| 40 | HC particulate |
| 45 | agent orange |
| 50 | a component of DS2 contaminant |

The array is finished up by nine empty pixels.

Figure 14A:
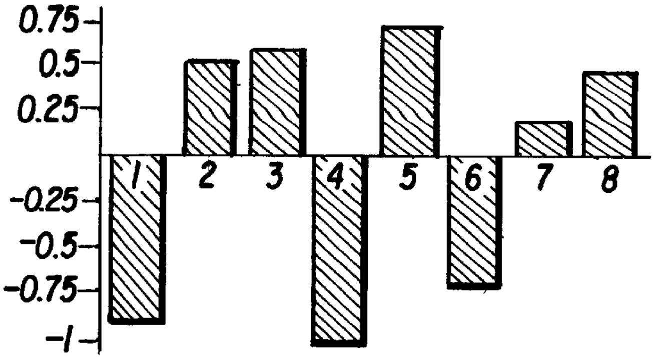
FIG. 14A shows the optimum linear discriminant for discriminating the signature of Sarin from the other signatures in FIG. 13A.
Figure 14B:
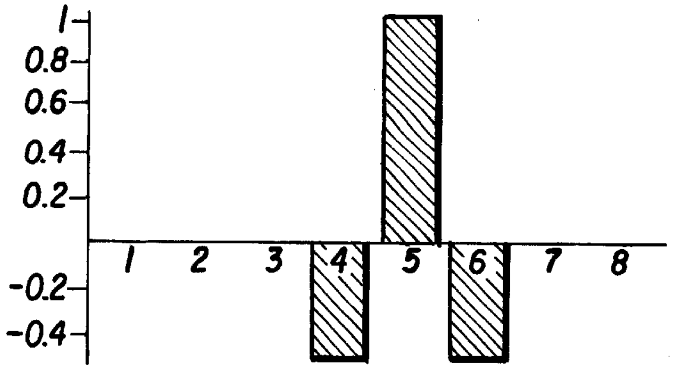
FIG. 14B shows a quasi-optimum linear discriminant for detecting the signature of Sarin, chosen by visual inspection of the signatures of FIG. 13A.

The first-step response for all ten compounds is obtained by taking the dot product of the LD's shown in FIGS. 14A and 14B with the 59 $\Delta^2L$ signatures shown in FIG. 16. The results in FIG. 17A show that the response to discrimination-optimized LD is just above the noise level for Sarin and a few other compounds. The results in FIG. 1713 show that the response to detection-optimized LD is well above the noise not only for Sarin, but also for most of the other compounds. Given that the primary goal of the first step is detection, the detection-optimized LD will be used, and discrimination will be reserved for the second step. (These results notwithstanding, it is still probable that some minimal discrimination could be accomplished at the first step if there are only a few interfering compounds not too spectrally similar to the threat.)

Figure 18:
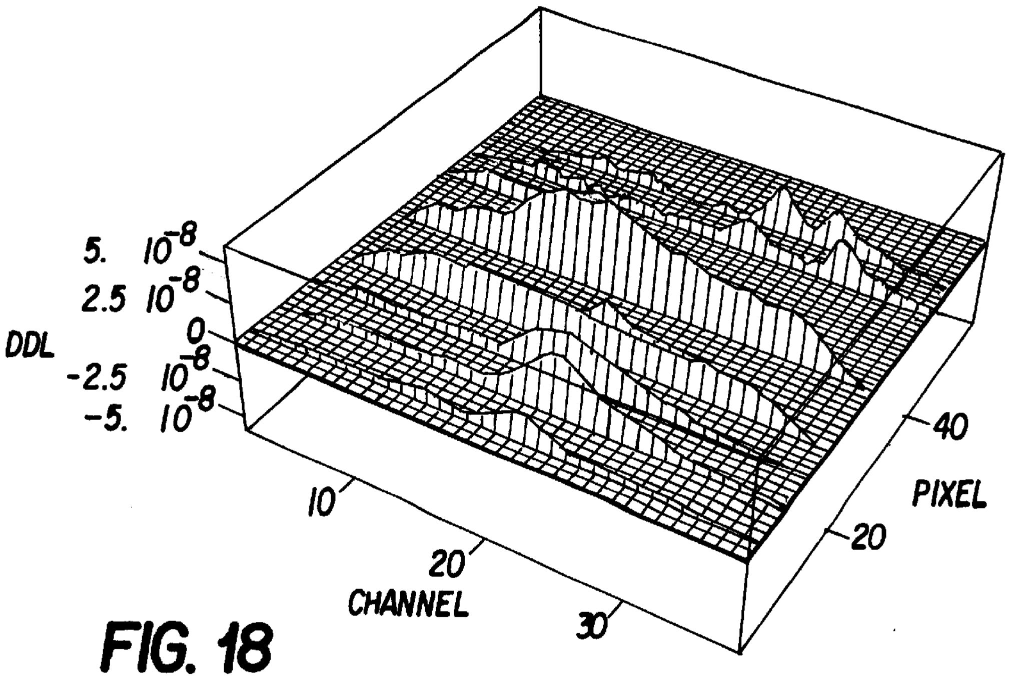
FIG. 18 shows a differential spectral radiance for the same mixture of ten compounds and Gaussian spectral noise as in FIG. 16 for 59 FOV's at a resolution of 16 $cm^{-1}$ and a measurement time of 1 sec.

Because a suspicious event is detected either the signal processor or the operator makes a decision to check further. The sensor rescans either the total FOV or some selected portion thereof at a higher resolution of 16 $cm^{-1}$ and a slower speed of 1 sec measurement time for each pixel (60 sec for all 60 pixels). FIG. 18 shows the $\Delta^2L$ signature array for the same ten components at the 16 $cm^{-1}$ resolution and the 1 sec measurement time.

Figure 15:
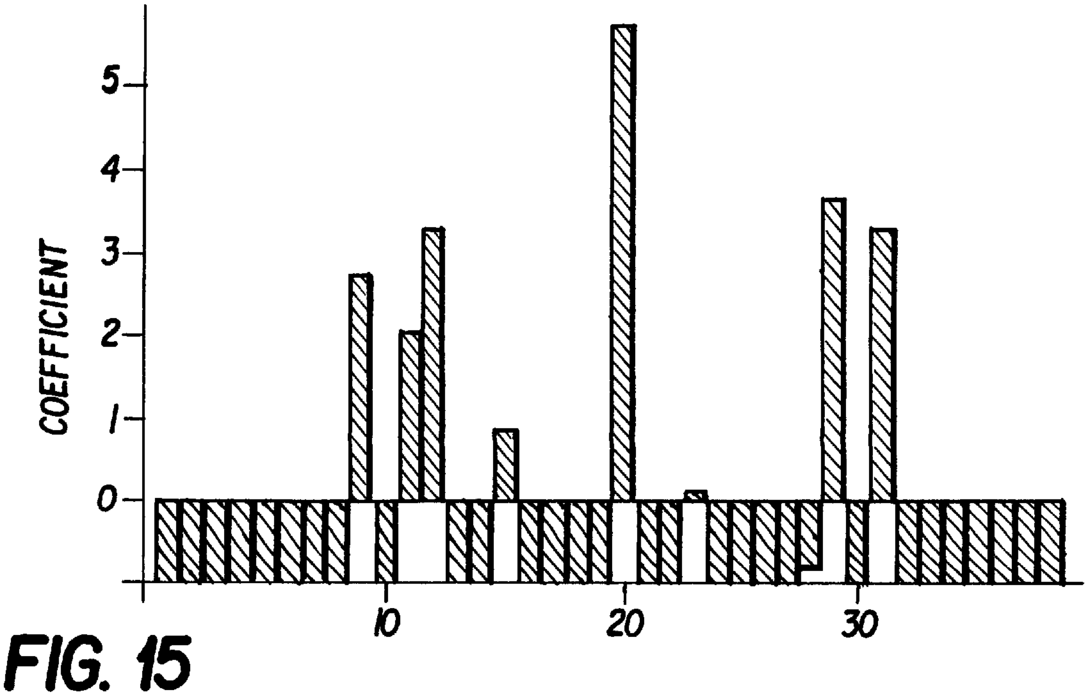
FIG. 15 shows an optimum linear discriminant for discriminating the signature of Sarin from the other signatures shown in FIG. 13B.

FIG. 19 shows the response curve for these signatures with the LD shown in FIG. 15. Only Sarin is detected; the response to all other compounds is below the noise level. The response curves shown in FIGS. 17A, 17B and 19 may be viewed as a single line in the raster scan of an imaging interferometer. A relatively high-speed image could be created by changing the AOE to produce a new line. Each line would be self-contained; the image would be formed by plotting contiguous raster lines.

Now that the principles underlying the invention are understood, an implementation of the invention will be described with reference to FIG. 20, which shows hazardous cloud imager (HAZCI) 1. HAZCI 1 includes horizontal scanning mirror 3 with horizontal scanning motor 5, vertical scanning mirror 7 with vertical scanning motor 9, objective lens 11, interferometer 13, detector array 15 having one to four detectors, signal processor 17, and personal computer (or other interface device) 19 with display screen (or other visual output device, such as a printer) 21 and keypad (or other input device) 23.

Horizontal scanning mirror 3 is pivoted about a vertical axis by horizontal scanning motor 5 to form a horizontal scan, which in an illustrative embodiment can be about sixty degrees. This mirror, or vertical scanning mirror 7 under control of vertical scanning motor 9, can also rotate about a horizontal axis, such as in increments of eight degrees, to form the vertical dimension of the image. The mirrors direct the radiant energy of the image to objective lens (or mirror) 11, which focuses the radiant energy into interferometer 13. A 2.5 cm (1") lens should suffice for operation up to 4 or 5 km. For each additional 5 km, 2.5 cm should be added to the diameter of the objective lens; for example, operation at 50 km should preferably use an objective of 25 cm (10").

Interferometer 13 can be a classical Michelson interferometer. This interferometer is easily designed to change resolution under control of a computing device such as signal processor 17; such a change in resolution is important in the two-step process of detection (at a low resolution such as 64 $cm^{-1}$) and discrimination (at a higher resolution such as 16 $cm^{-1}$). The usable aperture can be as small as 2 mm for 16 $cm^{-1}$ resolution.

In detector array 15, using at least two detectors in tandem offers several advantages. The difference signal between the two detectors will be much smaller than either signal alone, thereby substantially reducing the required dynamic range and the associated A/D and data handling problems. Two detectors would also speed up the scanning process. Because of the round aspect of the interferometer image, four detectors would be as acceptable as two, which would further speed up the scanning process, but at the cost of increasing the complexity.

The signal processor 17 applies the detection and discrimination algorithm, controls the sensor array 15, creates the image for display on display 21, and alerts the operator if a detection is made. To produce an array of difference ($\Delta^2L$) spectral signatures that contain only the information needed for the detection and identification of hazardous vapors or aerosols, a two-step operation with automatic first step detection and second step discrimination is employed, and false color images are used to enhance operator discrimination.

As will be explained in greater detail below, the signal processor 17 triggers a warning in the event that a hazardous cloud is detected, so as to alert the operator to evaluate the image in greater detail. The image, or portions of the image, are searched using the discrimination mode. The final decision can be made by the operator in accordance with the discriminated image of the cloud and all other information available to the operator or can be automated.

Figure 21:
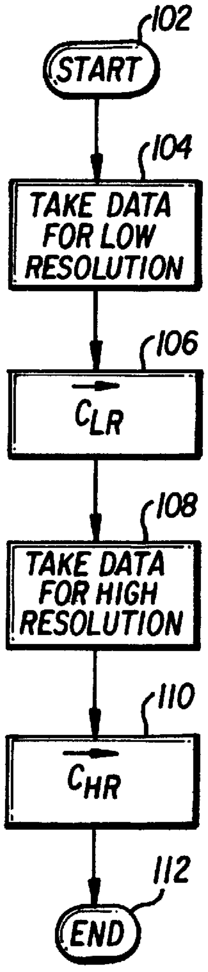
FIG. 21 shows a flow chart of operations used in training the apparatus of FIG. 20.

FIG. 21 shows a flow chart in which HAZCI is trained, namely, in which the linear discriminants are derived. In this example two linear discriminants are derived: a first linear discriminant CLR for detection at a low resolution and a second linear discriminant HR for discrimination at a high resolution. The training starts in step 102. In step 104, $\Delta^2$L spectral data are taken at low resolution for the threat and the interferents, as described above. In step 106, the spectral data taken in step 104 are used to derive $c_{LR}$ by linear programming or by another suitable technique. In step 108, the $\Delta^2$L spectral data are taken at high resolution for the threat and the interferents. In step 110, the spectral data taken in step 108 are used to derive $c_{HR}$. The training ends in step 112. This series of operations can be performed in the signal processor 17 or in another suitable device. Of course, the low- and high-resolution derivations do not have to be performed in that order; instead, the order cane reversed, or steps 104 and 106 can be performed in parallel with steps 108 and 110.

Figure 22:
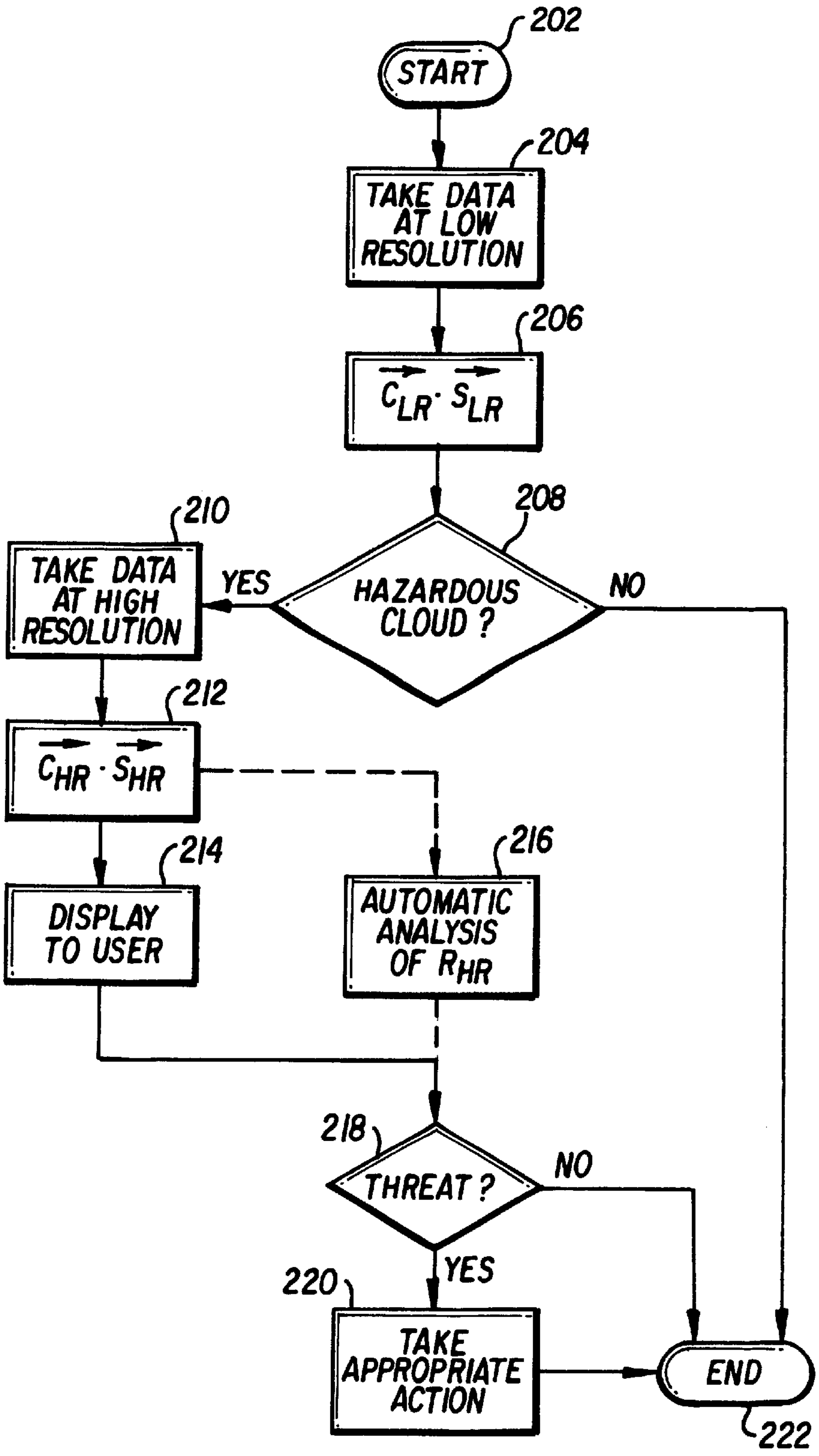
FIG. 22 shows a flow chart of operations used in detecting and discriminating a hazardous cloud with the apparatus of FIG. 20.

The linear discriminants derived in the operations of FIG. 21 are used as shown in FIG. 22, which shows a flow chart of detection and discrimination. The process of detection and discrimination starts in step 202. In step 204, $\Delta^2$L spectral data are taken at low resolution to form low-resolution spectral data vector SIR for each pixel. In step 206, the dot product of $s_{LR}$ with low-resolution linear discriminant $c_{LR}$ is taken to form low-resolution response $R_{LR}=s_{LR}\cdot c_{LR}$ for each pixel. This low-resolution response is examined in step 208, e.g., by comparing it to a threshold value, to detect a hazardous cloud.

If a hazardous cloud is detected in step 208, the discrimination phase begins. In step 210, the high-resolution data are taken to form high-resolution spectral data vector $s_{HR}$ for each pixel. In step 212, the dot product of $s_{HR}$ with high-resolution linear discriminant $c_{HR}$ is taken to form high-resolution response $R_{HR}=s_{HR}\cdot c_{HR}$ for each pixel. This response can be used to form a false-color image for display to the operator, as in step 214, or may be automatically analyzed, as in step 216. Either way, in step 218, the hazardous cloud is discriminated, it is determined whether the cloud is actually a threat and where the cloud is located. If the cloud is identified as a true threat, appropriate action is taken in step 220. Then, or if the detection in step 208 or the discrimination in step 218 yields a negative result, the process ends in step 222.

Figure 20:
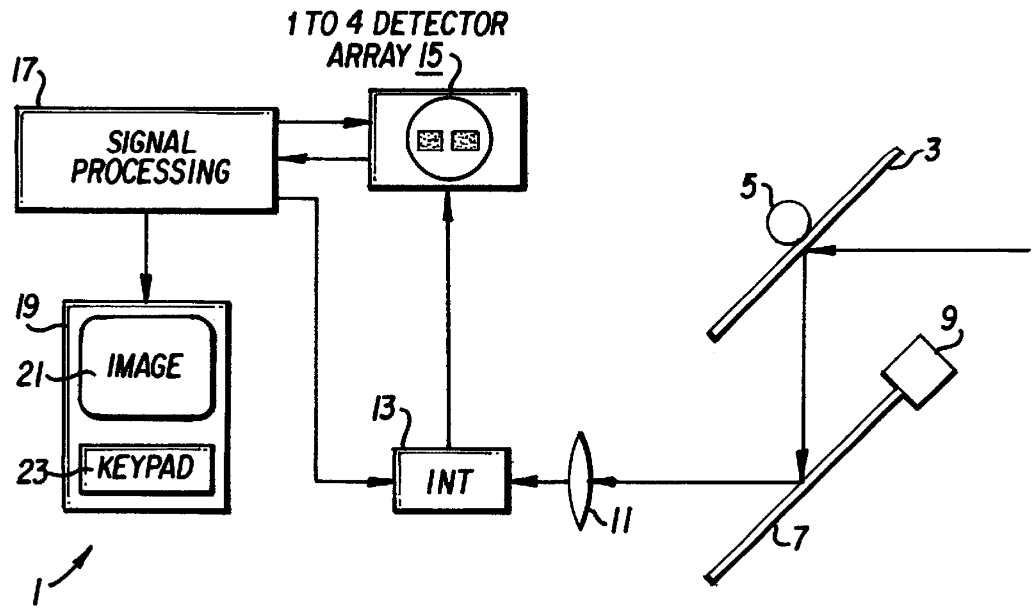
FIG. 20 shows an apparatus according to the present invention.

The HAZCI of FIG. 20 achieves a much larger field of view than has been accomplished in the prior art. FIG. 23 shows the 10°×60° FOV of the HAZCI of FIG. 20 in comparison with the 4°×6° FOV of a conventional FLIR system and the series of 1.50×1.5° FOV's, spaced center to center by 10°, of the M21.

Although the invention has been set forth with reference to a particular embodiment, it will be readily apparent to those skilled in the art who have reviewed this disclosure that other embodiments can be realized within the scope of the invention. For example, the operations described above can be implemented in any suitable hardware, software, or combination of hardware and software, and any appropriate mathematical operations can be employed. Also, modifications disclosed separately can be combined.

I claim:

1. A method of detecting and discriminating a hazardous cloud in a field of view, the method comprising:

(a) forming a first linear discriminant for detecting the hazardous cloud at a first spectral resolution and forming a second linear discriminant for discriminating the hazardous cloud at a second spectral resolution which is higher than the first spectral resolution;

(b) detecting the hazardous cloud by (i) taking a first $\Delta^2$L spectrum in the field of view at the first spectral resolution, (ii) applying the first linear discriminant to the first $\Delta^2$L spectrum to obtain a first response, and (iii) detecting whether the hazardous cloud is present in accordance with the first response; and (c) if the hazardous cloud is detected to be present in step (b)(iii), discriminating the hazardous cloud by (i) taking a second $\Delta^2$L spectrum in the field of view at the second spectral resolution, (ii) applying the second linear discriminant to the second $\Delta^2$L spectrum to obtain the second response; and (iii) discriminating the hazardous cloud in accordance with the second response.

2. The method of claim 1, wherein step (b)(iii) is performed automatically in a signal processing device.

3. The method of claim 2, wherein step (c)(iii) comprises:

(A) forming an image of the second response;

(B) displaying the image of the second response to an operator; and (C) receiving an input from the operator regarding the hazardous cloud.

4. A method of claim 1, wherein step (a) comprises forming the first and second linear discriminants from known spectral data for a plurality of materials by linear programming.

5. The method of claim 4, wherein step (a) comprises forming the first and second linear discriminants such that they give a non-zero response for a first of the plurality of materials and a substantially zero response for all of the plurality of materials except for the first of the plurality of materials.

6. The method of claim 1, wherein the first and second spectral resolutions are no higher than 16 $cm^{-1}$.

7. The method of claim 6, wherein:

the first spectral resolution is 64 $cm^{-1}$; and the second spectral resolution is 16 $cm^{-1}$.

8. The method of claim 1, wherein each of steps (b)(i) and (c)(i) comprises making a plurality of horizontal scans within the field of view, each of the horizontal scans at a different angle of elevation.

9. A system for detecting and discriminating a hazardous cloud in a field of view, the system comprising:

detector means for (i) taking a first $\Delta^2$L spectrum in the field of view at a first spectral resolution and (ii) taking a second $\Delta^2$L spectrum in the field of view at a second spectral resolution which is higher than the first spectral resolution;

signal processor means, said processor means storing a first linear discriminant for detecting the hazardous cloud at a first spectral resolution and a second linear discriminant for discriminating the hazardous cloud at a second spectral resolution which is higher than the first spectral resolution, for (i) detecting the hazardous cloud by applying the first linear discriminant to the first $\Delta^2$L spectrum to obtain a first response and detecting whether the hazardous cloud is present in accordance with the first response and (ii) if the hazardous cloud is detected to be present, discriminating the hazardous cloud by applying the second linear discriminant to the second $\Delta^2$L spectrum to obtain the second response and discriminating the hazardous cloud in accordance with the second response; and interface means for communicating to an operator a result of at least one of detecting and discriminating the hazardous cloud.

10. The system of claim 9, wherein:

the signal processing means comprises means for forming an image of the second response; and the interface means comprises means for displaying the image of the second response to the operator under control of the signal processing means.

11. The system of claim 10, wherein the interface means further comprises means for receiving an input from the operator.

12. The system of claim 11, wherein the hazardous cloud is detected automatically in the signal processing means.

13. The system of claim 12, wherein the hazardous cloud is discriminated by displaying the image to the operator, allowing the operator to make the input indicating discrimination of the hazardous cloud, and receiving from the operator the input.

14. The system of claim 9, wherein the signal processing means comprises means for forming the first and second linear discriminants from known spectral data for a plurality of materials by linear programming.

15. The system of claim 14, wherein the means for forming forms the first and second linear discriminants such that they give a non-zero response for a first of the plurality of materials and a substantially zero response for all of the plurality of materials except for the first of the plurality of materials.

16. The system of claim 9, wherein the first and second spectral resolutions are no higher than 16 $cm^{-1}$.

17. The system of claim 16, wherein:

the first spectral resolution is 64 $cm^{-1}$; and the second spectral resolution is 16 $cm^{-1}$.

18. The system of claim 9, wherein the detecting means comprises means for taking each of the first and second $\Delta^2 L$ spectra by making a plurality of horizontal scans within the field of view, each of the horizontal scans at a different angle of elevation.

19. The system of claim 18, wherein the means for taking comprises a horizontal scanning mirror and a vertical scanning mirror.

20. The system of claim 9, wherein the detecting means comprises an interferometer.

21. The system of claim 20, wherein the interferometer is a Michelson interferometer.

22. The system of claim 20, wherein the detecting means further comprises an array of at least two detector elements.

23. The system of claim 22, wherein the array comprises four detector elements.

* * * * *